United States Patent [19]

Campbell et al.

[11] Patent Number: 4,898,872

[45] Date of Patent: Feb. 6, 1990

[54] IMIDAZO[4,5-B]PYRIDYL QUINOLONE CARDIAC STIMULANTS

[75] Inventors: Simon F. Campbell, Grey Friars; David S. Morris, Westgate-on-Sea; David A. Roberts, Congleton, all of England

[73] Assignee: Pfizer Inc., New York, N.Y.

[21] Appl. No.: 184,462

[22] Filed: Apr. 21, 1988

[30] Foreign Application Priority Data

Apr. 21, 1987 [GB] United Kingdom ............... 8709448

[51] Int. Cl.[4] ............... A61K 31/47; C07D 471/04
[52] U.S. Cl. ............... 514/303; 544/237; 546/118; 546/141; 546/157; 546/158
[58] Field of Search ............... 514/303; 546/118

[56] References Cited

U.S. PATENT DOCUMENTS

| | | | |
|---|---|---|---|
| 4,710,507 | 12/1987 | Campbell et al. | 514/312 |
| 4,728,653 | 3/1988 | Campbell et al. | 514/312 |
| 4,728,654 | 3/1988 | Campbell et al. | 514/312 |
| 4,740,513 | 4/1988 | Campbell et al. | 546/157 |

FOREIGN PATENT DOCUMENTS 0052016 5/1982 European Pat. Off. .

*Primary Examiner*—Mary C. Lee
*Assistant Examiner*—Bernard I. Dentz
*Attorney, Agent, or Firm*—Peter C. Richardson; Paul H. Ginsburg

[57] ABSTRACT

A series of novel heterobicyclic substituted 2-(1H)-quinolone compounds have been prepared, including the 3,4-dihydro derivatives thereof, wherein the heterobicyclic ring moiety is an optionally-substituted indolyl, phthalizinyl, benzimidazolyl, imidazopyridinyl, quinolinyl or isoquinolinyl group attached by an nitrogen or carbon atom of said group to the 6-position of the quinolone ring. The optional substituent is a $C_1$–$C_{14}$ alkyl group located on either of the two heterobicyclic rings and/or an oxo group situated on the heterocyclic portion of said heterobicyclic ring system. These particular compounds are useful in therapy as cardiac stimulants and therefore, are of value in the treatment of various cardiac conditions. 6-{1(H)-Imidazo[4,5-b]pyridin-6-yl}-8-methyl-2-(1H)-quinolone represents a typical and preferred member compound. Methods for preparing these compounds from known starting materials are provided.

10 Claims, No Drawings

IMIDAZO[4,5-B]PYRIDYL QUINOLONE CARDIAC STIMULANTS

BACKGROUND OF THE INVENTION

The present invention relates to substituted quinolone cardiac stimulants which in general selectively increase the force of myocardial contraction without producing significant increases in the heart rate. The compounds are useful in the curative or prophylactic treatment of cardiac conditions, in particular heart failure.

SUMMARY OF THE INVENTION

Thus according to the present invention there are provided substituted quinolone compounds of the formula (I):

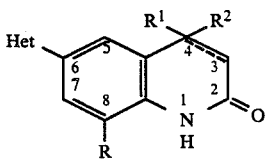

and their pharmaceutically acceptable salts, wherein
Het represents a heterobicyclic group having a 6-membered ring fused to a further 5 or 6 membered ring, containing from 1 to 3 N-atoms in the non-fused positions, attached by a nitrogen or carbon atom to the quinolone and optionally substituted in one or both of the rings with one or more $C_{1-4}$ alkyl groups and/or an oxo group; p0 R is hydrogen or $C_{1-4}$ alkyl;
$R^1$ and $R^2$ are each independently H or $C_{1-4}$ alkyl and the dashed line between the 3- and 4-positions represents an optional bond in which case $R^2$ is absent.

Het is for example a group selected from indolinyl, phthalazinyl, benzimidazolyl, imidazopyridinyl, quinolinyl or isoquinolinyl groups.

The preferred substituents for Het are methyl and oxo.

Particularly preferred groups are benzimidazol-2-yl optionally substituted with up to 3 methyl groups, 2-oxo-benzimidazol-1-yl, 2-methyl-benzimidazol-1-yl, 4-oxo-phthalazin-1-yl, 8-methyl-2-oxo-quinolin-6-yl, 3,3-dimethyl-2-oxo-indolin-5-yl, (1H)-imadazo[4,5-b]pyridin-6-yl, 2-oxo-imidazo[4,5-b]pyridin-6-yl or isoquinoline-4-yl.

The most preferred individual compound of the formula (I) has the formula:

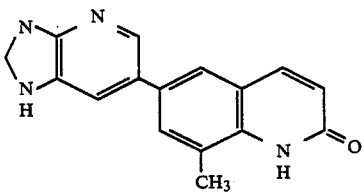

i.e. R is methyl, Het is (1H)-imidazo[4,5-b]pyridin-6yl, $R^1$ is H and there is a double bond between the 3- and 4-positions of the quinoline ring.

Although the compounds of the formula (I) are written as 2-(1H)-quinolones, it should be realised that the following tautomerism will occur:

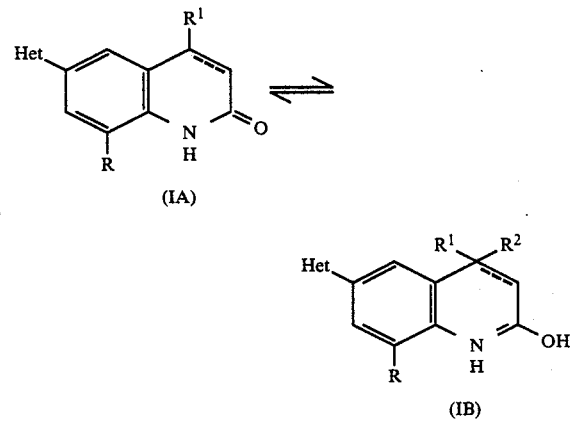

However, as the keto-form is considered the more stable tautomer, the end products herein will be named and illustrated as quinolones although those skilled in the art will realise that both tautomers may be present or that any particular compound so named may exist predominantly as the hydroxy tautomer and the following disclosure is to be interpreted to incorporate all tautomeric forms.

Preferably there is a double bond in the 3,4-position. R, $R_1$ and $R_2$ are preferably H or $CH_3$. R is most preferably $CH_3$.

The pharmaceutically acceptable salts of the compounds of the formula (I) are either acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, methanesulphonate and p-toluenesulphonate salts, or are metal salts, particularly the alkaline earth or alkali metal salts. The preferred metal salts are the sodium and potassium salts. All the salts are preparable by conventional techniques.

Accordingly, the present invention comprises heterobicyclic-substituted 2-(1H)-quinolone compounds of the formulae:

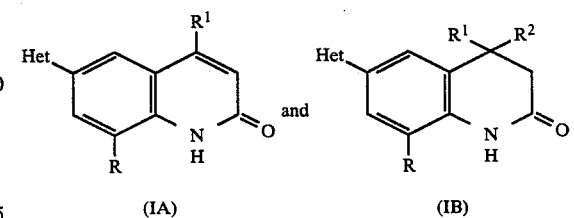

and the pharmaceutically acceptable salts thereof, wherein Het, R, $R^1$ and $R^2$ are each as previously defined.

One group of preferred compounds of the present invention includes those of formula (IA) wherein Het is 3,3-dimethyl-2-oxoindolin-5-yl, 4-oxophthalazin-1-yl, 2-methylbenzimidazol-1-yl, 2-oxobenzimidazol-1-yl, benzimidazol-2-yl, 1-methylbenzimidazol-2-yl, 1,5,6-trimethylbenzimidazol-2-yl, benzimidazol-5(6)-yl, 1(H)-imidazo[4,5-b]pyridin-6yl, 2-oxoimidazo[4,5-b]-pyridin-6-yl, 8-methyl-2-oxoquinolin-4-yl or isoquinolin-4-yl; and R and $R^1$ are each hydrogen or methyl. Especially preferred compounds within this category include those where R is methyl and $R^2$ is hydrogen.

Another group of preferred compounds of the present invention includes those of formula (IB) wherein Het is benzimidazol-1-yl, 2-methylbenzimidazol-1-yl or 2-oxobenzimidazol-1-yl; R is methyl, and $R^1$ and $R^2$ are each hydrogen or methyl. Especially preferred compounds within this category include those where $R^1$ is methyl and $R^2$ is hydrogen.

The cardiac stimulant activity of the compounds of the formula (I) is shown by their effectiveness in one or more of the following tests: (a) increasing the force of contraction in the "Starling" dog heart-lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog heart-lung preparation. The selectivity for increase in force versus frequency of contraction of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the formula (I) can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the invention will be in the range from 10 mg to 1 g daily, taken in up to 4 divided doses per day, for an average adult patient (70 kg). Dosages for intravenous administration would be expected to be within the range 0.5 to 100 mg per single dose as required, for example in the treatment of acute heart failure. Thus for a typical adult patient, individual tablets or capsules might contain 2.5 to 250 mg of active compound, in a suitable pharmaceutically acceptable vehicle or carrier.

Variations may occur depending on the weight and condition of the subject being treated as will be known to medical practitioners. Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of a human being, which comprises administering to said human a compound of formula (I) or pharmaceutically acceptable salt thereof, or a pharmaceutical composition as defined above, in an amount sufficient to stimulate the heart of said human.

The invention yet further provides a compound of the formula (I) or pharmaceutically acceptable salt thereof, for use in medicine, in particular for use in stimulating the heart of a human being suffering from congestive heart failure.

DETAILED DESCRIPTION OF THE INVENTION

The compounds of the formula (I) can be prepared by a number of routes, including the following:

Route A

This route can be illustrated in general terms as follows:

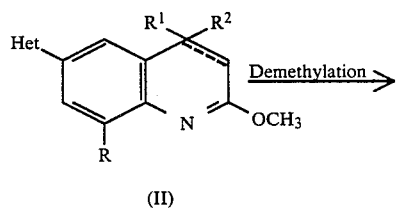

(II)

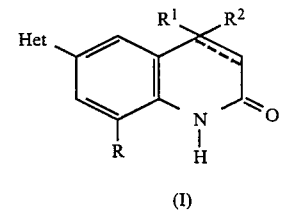

(I)

The demethylation is preferably carried out by heating the methoxyquinoline (II) in aqueous mineral acid, preferably aqueous HCl or HBr, and typically in 5M aqueous HCl or 48% aqueous HBr at up to reflux temperature, generally for 0.5–4 hours. Alternatively it is carried out by heating at up to reflux temperature in ethanol containing at least one equivalent (generally 5–15% by volume) of 48% aqueous HBr. The product can then be isolated and purified by conventional means.

A typical reaction using 5M HCl is illustrated as follows:

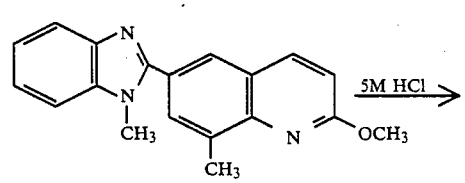

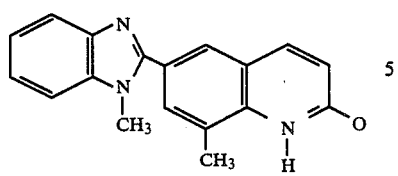

A typical reaction using 48% aqueous HBr is illustrated as follows:

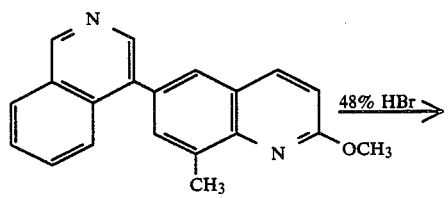

A typical reaction using ethanol containing at least one equivalent of 48% HBr is illustrated as follows:

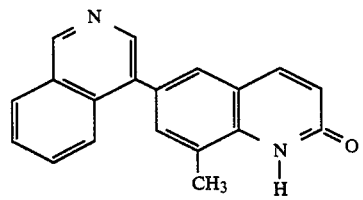

The starting materials of the formula (II) can be prepared by conventional procedures. Typical general routes to these materials, many of which are illustrated in detail in the following Preparations are as follows:

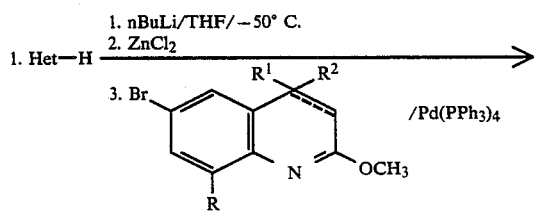

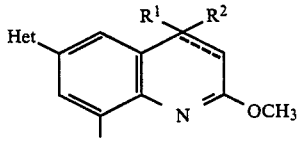

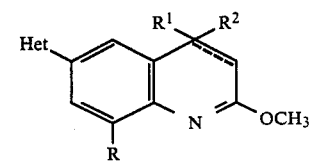

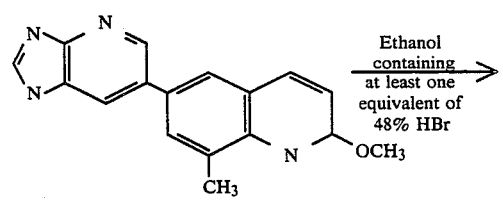

When it is required to prepare compounds wherein Het is substituted with an oxo group this may be achieved by use of a starting material containing a methoxy group which can subsequently be demethylated. Thus demethylation can be effected in both Het and the quinoline moiety simultaneously.

Route B

This route can be illustrated in general terms as follows:

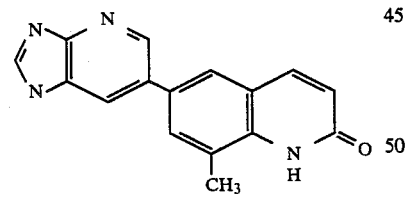

where Q is a leaving group such as $C_1$-$C_4$ alkoxy.

The cyclisation is preferably carried out by treating the propenamide (III) with concentrated, desirably substantially anhydrous (98%), sulphuric acid at room temperature until the reaction is complete, typically in 6–48 hours. If necessary, heating at up to 100° C. can be carried out to speed up the reaction. The product can then be isolated and purified by conventional procedures. In the propenamide (III), Q is preferably ethoxy or methoxy.

The propenamide (III) can also be used in acid addition salt form.

A typical reaction is illustrated as follows:

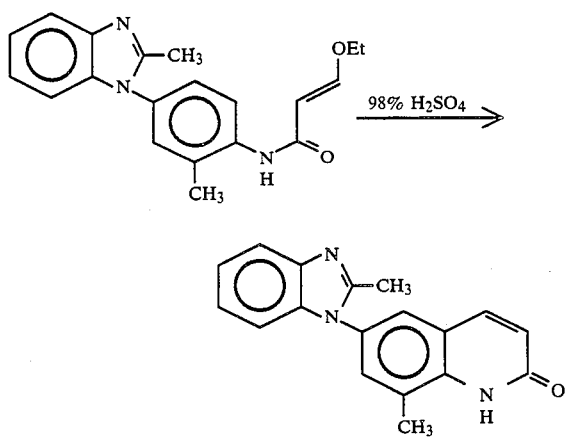

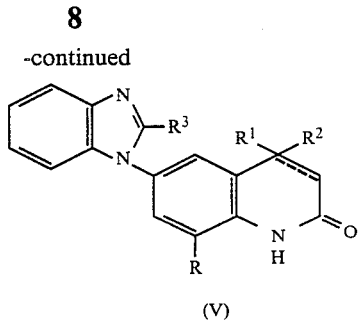

The starting materials of the formula (III) can be prepared by conventional procedures. A typical route to these materials, many of which are illustrated in detail in the following Preparations, is as follows:

where $R^3$ is hydrogen or $C_1$–$C_4$ alkyl.

The reaction involves the condensation of a diaminobenzene of formula IV with a carboxylic acid to form the correspondingly substituted benzimidazole.

This reaction is typically carried out by heating the diaminobenzene of formula IV in the appropriate carboxylic acid, desirably acetic acid, at a temperature up to reflux for 1–12 hours. The product can then be isolated and purified conventionally.

A typical reaction may be illustrated as follows:

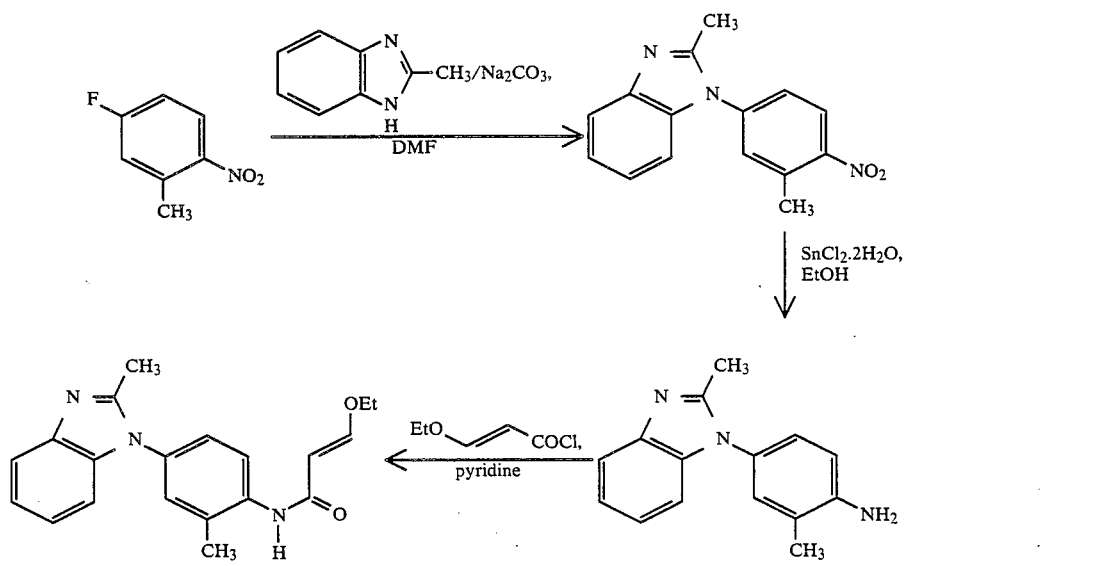

Route C

This route can be illustrated in general terms as follows:

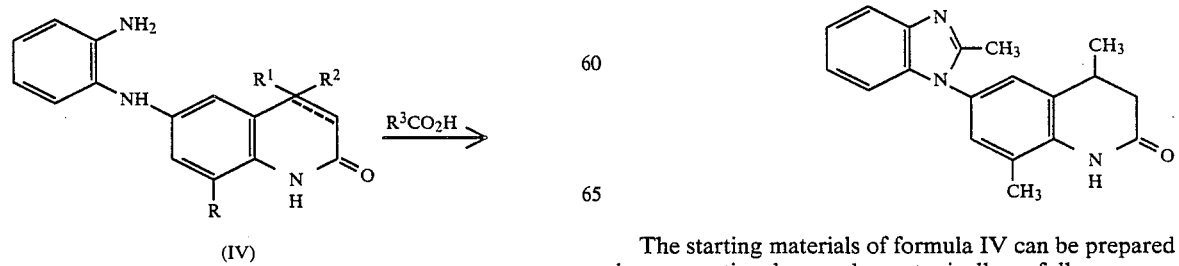

The starting materials of formula IV can be prepared by conventional procedures, typically as follows:

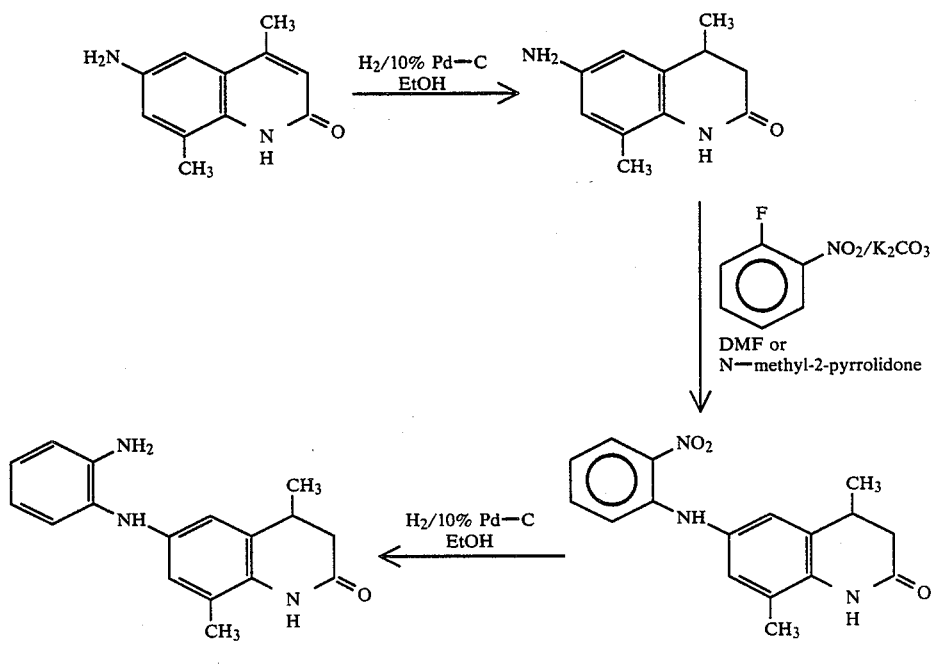

Route D

This route may be illustrated in general termss as follows:

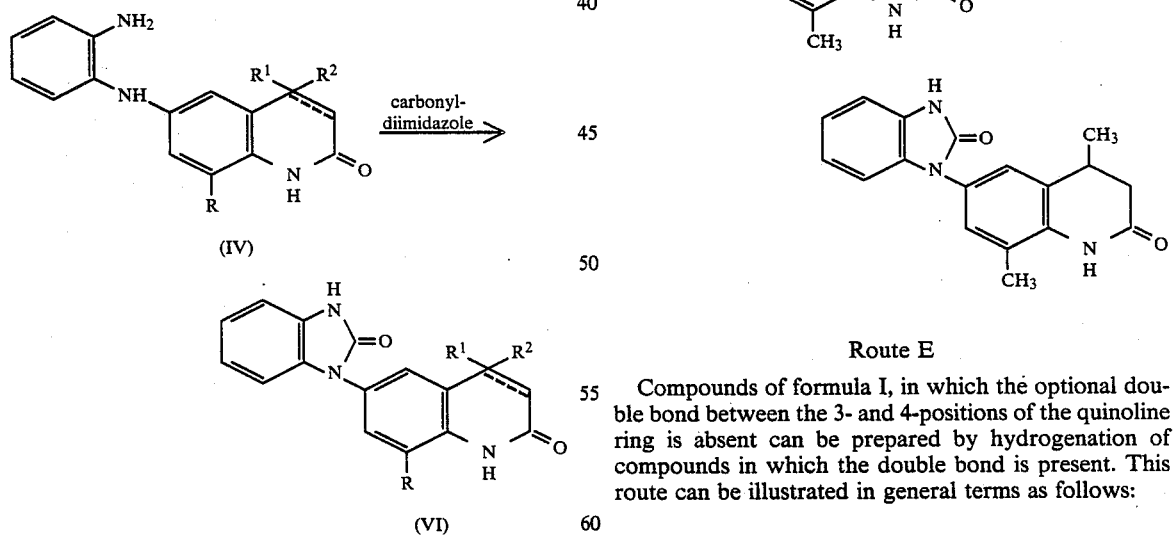

This reaction involves the condensation of a diaminobenzene of formula IV with carbonyldiimidazole in a suitable solvent, typically tetrahydrofuran (THF) at temperatures ranging from 0° C. up to reflux temperature for 0.5 to 4 hours. The product can be isolated and purified by conventional procedures.

A typical reaction may be illustrated as follows:

Route E

Compounds of formula I, in which the optional double bond between the 3- and 4-positions of the quinoline ring is absent can be prepared by hydrogenation of compounds in which the double bond is present. This route can be illustrated in general terms as follows:

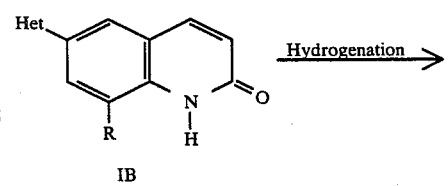

-continued

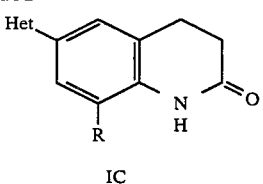
IC

The reaction is typically carried out by hydrogenation of the starting material (IB) in a suitable organic solvent (e.g. ethanol) over a transition metal catalyst (e.g. 5-10% palladium on charcoal or platinum oxide) at 1-330 atmospheres pressure and at up to 100° C.

Where the compounds of the invention contain one or more asymmetric centres, then the invention includes the separated enantiomers and diastereoisomers or mixtures thereof. The separated forms can be obtained by conventional means.

The following Examples illustrate the invention (all temperatures are in °C.):

EXAMPLE 1

6-(1,5,6-Trimethylbenzimidazol-2-yl)-8-methyl-2-(1H)-quinolone, 0.25 H₂O

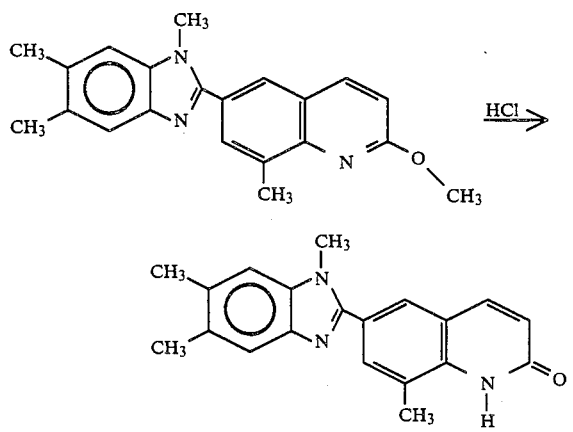

2-Methoxy-6-(1,5,6-trimethylbenzimidazol-2-yl)-8-methylquinoline (0.5 g) was added with stirring to hydrochloric acid (20 cm³ of a 5M aqueous solution) at room temperature (20°). The mixture was heated under reflux for 2 hours, cooled, poured into water (20 cm³), basified to pH9 with sodium carbonate solution, and extracted with methanol:dichloromethane (1:20 by volume, 2×100 cm³). The combined and dried (MgSO₄) organic extracts were evaporated in vacuo to give a solid which was recrystallised from ethyl acetate/methanol to afford the title compound, m.p. 314°-6° (0.35 g).

Analysis %: Found: C, 74.4; H, 6.3; N, 12.9; Calculated for $C_{20}H_{19}N_3O$, 0.25 H₂O: C, 74.6; H, 6.1; N, 13.0.

EXAMPLES 2-7

The following compounds (Formula IB) were prepared similarly to the procedure of Example 1 using the appropriate heterobicyclic substituted quinolone and hydrochloric acid as starting materials:

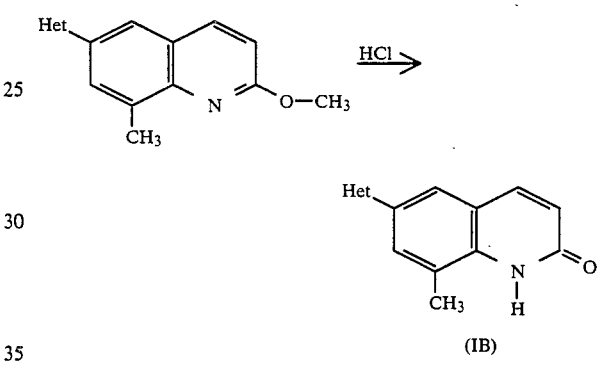

| Example No. | Het | Form Isolated and m.p. (°C.) | Analysis % (Theoretical in brackets) | | |
|---|---|---|---|---|---|
| | | | C | H | N |
| 2 | benzimidazol-2-yl (NH) | Free base 1.5 H₂O 317.5-319° | 68.6 (68.6 | 5.1 5.1 | 13.9 14.1) |
| 3 | 1-methyl-2-oxo-benzimidazol-3-yl | Free base 322° (d) | Characterised spectroscopically | | |
| 4 | 1-methylbenzimidazol-2-yl | Free base 0.25 H₂O 266-8° | 74.0 (73.6 | 5.2 5.3 | 14.1 14.3) |

| Example No. | Het | Form Isolated and m.p. (°C.) | Analysis % (Theoretical in brackets) | | |
|---|---|---|---|---|---|
| | | | C | H | N |
| 5 | (phthalazinone-methyl structure) | Free base H₂O >330° | 67.4 (67.3 | 4.4 4.7 | 12.6 13.1) |
| 6 | (8-methyl-6-methyl quinolinone structure) | Free base 0.33 H₂O >335° | 74.3 (74.5 | 5.1 5.4 | 8.6 8.7) |
| 7 | (3,3-dimethyl-oxindole methyl structure) | Free base 0.33 H₂O >310° | 74.1 (74.1 | 5.8 5.7 | 8.6 9.2) |

EXAMPLE 8

6-{(1H)-Imidazo[4,5-b]pyridin-6-yl)}-8-methyl-2-(1H)-quinolone, dihydrobromide, 2 H₂O

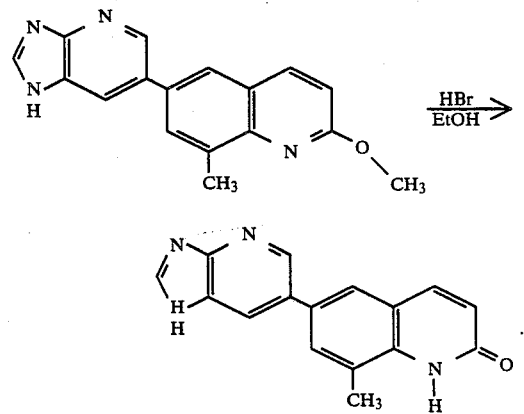

2-Methoxy-6-(1H)-imidazo-[4,5-b]-pyridin-6-yl)-8-methylquinoline (0.13 g) was added with stirring to a solution of hydrobromic acid (1 cm³ of a 60% aqueous solution) in absolute ethanol (10 cm³) at room temperature (20°). The mixture was heated under reflux for 5 hours, cooled and filtered to give the title compound, m.p. >350° (0.07 g).

Analysis %: Found: C, 40.5; H, 3.3; N, 11.4; Calculated for C₁₆H₁₂N₄O.2HBr.2H₂O: C, 40.5; H, 3.8; N, 11.8.

EXAMPLES 9–10

The following compounds (Formula IB) were prepared similarly to the procedure of Example 8 using the appropriate heterocyclic-substituted quinolone and hydrobromic acid as starting materials.

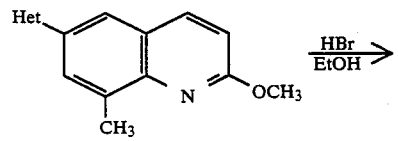

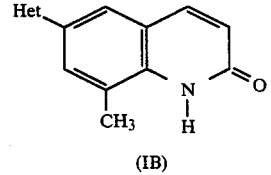

(IB)

| Example No. | Het | Form Isolated and m.p. (°C.) | Analysis % (Theoretical in brackets) | | |
|---|---|---|---|---|---|
| | | | C | H | N |
| 9 | (benzimidazole methyl structure) | Hydrobromide salt 0.25 H₂O >350° | 56.4 (56.5 | 3.9 4.0 | 11.3 11.6) |

| Example No. | Het | Form Isolated and m.p. (°C.) | Analysis % (Theoretical in brackets) C | H | N |
|---|---|---|---|---|---|
| 10 | 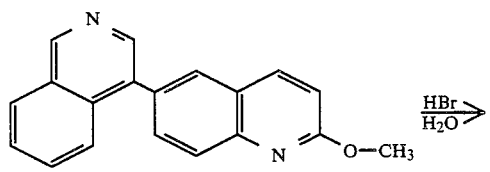 | Hydrobromide salt >350° | 51.6 (51.5 | 3.5 4.0 | 15.0 15.0) |

EXAMPLE 11

6-(Isoquinolin-4-yl)-2-(1H)-quinolone, 0.25 H$_2$O

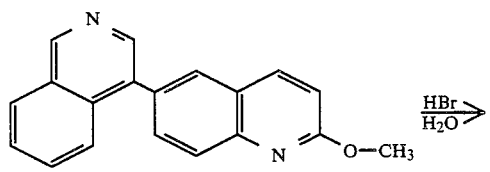

2-Methoxy-6-(Isoquinolin-4-yl)-quinoline (0.5 g) was added with stirring to hydrobromic acid (5 cm$^3$ of a 48% aqueous solution) at room temperature (20° C.). The mixture was heated under reflux for 3 hours, cooled, poured into water (10 cm$^3$), basified to pH 9 with sodium carbonate solution, and extracted with chloroform (4×50 cm$^3$). The combined and dried (MgSO$_4$) extracts were evaporated in vacuo to give a residue which was chromatographed on silica (Merck "MK 60.9385" [Trade Mark]) eluting with methanol:-chloroform, 1:20 by volume. Collection and evaporation of appropriate fractions afforded a foam which on trituration with ethyl acetate gave the title compound, m.p. 248°-51° (0.43 g).

Analysis %: Found: C, 77.9; H, 4.5; N, 9.9; Calculated for C$_{18}$H$_{12}$N$_2$O, 0.25 H$_2$O: C, 78.1; H, 4.6; N, 10.1.

EXAMPLE 12

6-(2-Methylbenzimidazol-1-yl)-8-methyl-2-(1H)-quinolone

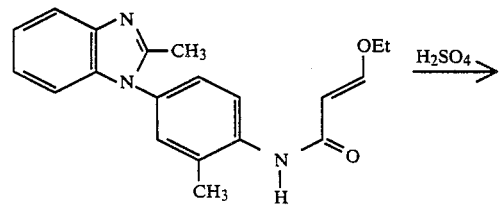

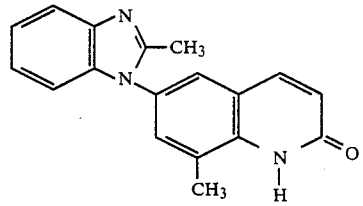

Trans-1-{4-[N-(3-ethoxypropenamido)]-3-methylphenyl}-2-methylbenzimidazole (1.45 g) was added with stirring to 98% w/w sulphuric acid (10 cm$^3$) at 0° C. After 24 hours at room temperature (20°) the mixture was poured carefully onto ice (100 g) and the resulting solution was basified to pH9 with saturated sodium carbonate solution. The mixture was then extracted with methanol:chloroform, 1:20 by volume (3×200 cm$^3$), and the combined and dried (MgSO$_4$) organic extracts were evaporated in vacuo to give a residue which was chromatographed on silica (Merck "MK 60.9385" [Trade Mark]). Elution with methanol:dichloromethane, 1:50 by volume, followed by combination and evaporation of appropriate fractions gave a solid which was triturated with ethyl acetate to afford the title compound, m.p. 307°-313°, (0.42 g).

Analysis %: Found: C, 73.0; H, 5.3; N, 14.0; Calculated for C$_{18}$H$_{15}$N$_3$O: C, 72.5; H, 5.4; N, 14.1.

EXAMPLE 13

3,4-Dihydro-4,8-dimethyl-6-(2-methylbenzimidazol-1-yl)-2-(1H)-quinolone

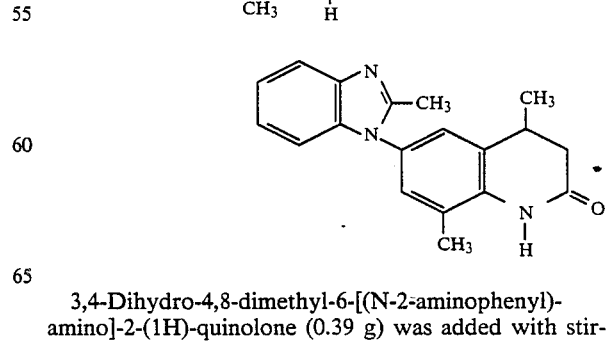

3,4-Dihydro-4,8-dimethyl-6-[(N-2-aminophenyl)-amino]-2-(1H)-quinolone (0.39 g) was added with stirring to glacial acetic acid (3 cm$^3$) and the mixture heated under reflux for 5 hours. Solvent was evaporated in vacuo and the residue partitioned between saturated sodium carbonate solution (40 cm³) and dichloromethane (50 cm³). The aqueous phase was separated and re-extracted with dichloromethane (2×50 cm³) and the combined and dried (MgSO₄) organic extracts were evaporated in vacuo to give a solid which was chromatographed on silica (Merck "MK 60.9385" [Trade Mark]). Elution with methanol:chloroform, 1:100 by volume followed by combination and evaporation at appropriate fractions gave a solid which was triturated with diethyl ether to afford the title compound, m.p. 248°–252°, (0.11 g).

Analysis %: Found: C, 73.8; H, 6.3; N, 13.6; Calculated for $C_{19}H_{19}N_3O$: C, 74.7; H, 6.3; N, 13.8.

EXAMPLE 14

3,4-Dihydro-4,4,8-trimethyl-6-(2-methylbenzimidazol-1-yl)-2-(1H)-quinolone, 0.25 H₂O This compound, m.p. 243°–246°, was prepared similarly to Example 13 using 3,4-dihydro-4,8,8-trimethyl-6-[(N-2-aminophenyl)amino]-2-(1H)-quinolone and acetic acid as starting materials:

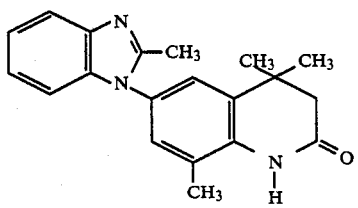

Analysis %: Found: C, 73.8; H, 6.7; N, 12.7; Calculated for $C_{20}H_{21}N_3O$, 0.25 H₂O: C, 74.2; H, 6.7; N, 13.0.

EXAMPLE 15

3,4-Dihydro-4,8-dimethyl-6-(benzimidazol-1-yl)-2-(1H)-quinolone, 0.25 H₂O

This compound, m.p. 198°–203°, was prepared similarly to Example 13 using 3,4-dihydro-4,8-dimethyl-6-[(N-2-aminophenyl)amino]-2-(1H)-quinolone as one starting material and formic acid (rather than acetic acid) as the other starting material.

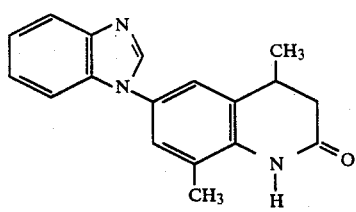

Analysis %: Found: C, 73.3; H, 5.9; N, 14.1; Calculated for $C_{18}H_{17}N_3O$, 0.25 H₂O: C, 73.1; H, 6.0; N, 14.2.

EXAMPLE 16

3,4-Dihydro-4,8-dimethyl-6-(2-oxobenzimidazol-1-yl)-2-(1H)-quinolone

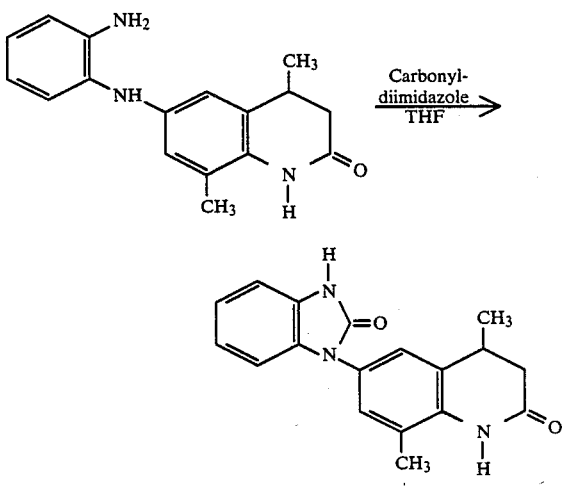

A solution of carbonyl diimidazole (0.33 g) in tetrahydrofuran (THF) (2 cm³) was added dropwise to a stirred solution of 3,4-dihydro-4,8-dimethyl-6-[(N-2-aminophenyl)amino]-2-(1H)-quinolone (0.24 g) in THF (2 cm³) at room temperature (20°). After 2 hours the solvent was evaporated in vacuo and the residue chromatographed on silica (Merck "MK 60.9385" [Trade Mark]) eluting with ethyl acetate. Collection and evaporation of appropriate fractions afforded a solid which was recrystallised from ethyl acetate to give the title compound, m.p. 250°–254° (0.13 g).

Analysis %: Found: C, 69.7; H, 5.7; N, 13.6; Calculated for $C_{18}H_{17}N_3O_2$: C, 70.3; H, 5.6; N, 13.7.

PREPARATION 1

2-Methoxy-6-{(1H)-imidazo-[4,5-b]pyridin-6-yl)}-8-methyl-quinoline

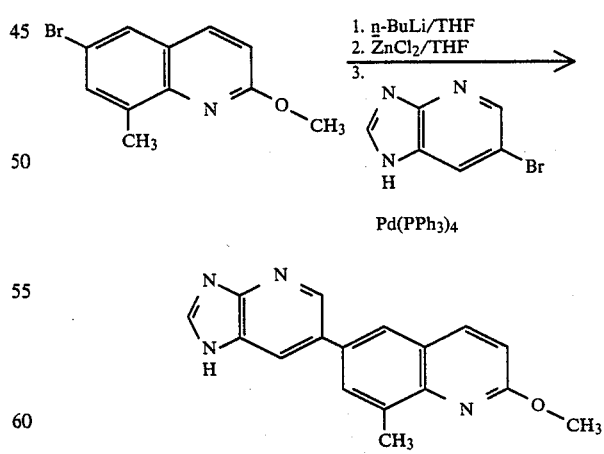

n-Butyllithium (5.5 cm³ of a 1.6M solution in hexane) was added dropwise to a stirred solution of 2-methoxy-6-bromo-8-methylquinoline (2.04 g) in tetrahydrofuran (THF) (50 cm³) at −70° under nitrogen. After 1 hour a solution of anhydrous zinc chloride (4.9 g) in THF (50 cm³) was added and the mixture was allowed to warm to room temperature. 6-Bromo-(1H)-imidazo-[4,5-b]pyridine (0.32 g) and tetrakis (triphenylphosphine)-palladium (O) (0.1 g) were added and the mixture heated under reflux for 24 hours. Saturated ammonium chloride solution (10 cm³) was added to the cooled mixture followed by a solution of ethylenediamine-tetraacetic acid disodium salt (12.0 g) in water (200 cm³). Ethyl acetate (200 cm³) and methanol (60 cm³) were added and the phases separated. The aqueous layer was further extracted with methanol:chloroform, 1:10 by volume (2×200 cm³), and the combined and dried (MgSO₄) organic extracts were evaporated in vacuo to afford a solid which was chromatographed on silica (Merck "MK 60.9385" [Trade Mark]) eluting with methanol:dichloromethane, 1:10 by volume. Combination and evaporation of appropriate fractions gave the desbromo quinoline starting material (0.92 g) and then the title compound (0.14 g) which was characterised spectroscopically and used without further purification in Example 8.

PREPARATIONS 2-7

The following compounds were prepared similarly to Preparation 1 using 2-methoxy-6-bromo-8-methyl-quinoline, n-butyllithium, zinc chloride and the appropriate bromoheterobicyclic compound as starting materials:

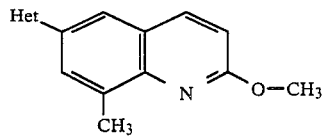

| Preparation No. | Het | Form Isolated and m.p. (°C.) | Analysis % (Theoretical in brackets) | | |
|---|---|---|---|---|---|
| | | | C | H | N |
| 2 | (benzimidazole structure) | Free base H₂O 199° | 70.8 (70.3 | 5.1 5.5 | 13.2 13.6) |
| 3 | (methoxy-methylquinoline structure) | Free base 205–207.5° | 76.4 (76.7 | 5.8 5.9 | 8.0 8.1) |
| 4 | (benzimidazolone structure) | Free base 0.75 H₂O >350° | 63.9 (63.9 | 4.5 4.9 | 17.4 17.5) |
| 5 | (dimethyl oxindole structure) | Free base 0.33 H₂O 239–242° | 75.0 (74.5 | 6.1 6.4 | 8.0 8.3) |
| 6 | (benzoyl hydrazone structure) | Free base 294–296° | 71.7 (71.9 | 4.9 4.8 | 12.8 13.2) |
| 7 | (iodoisoquinoline structure) | Characterised spectroscopically | | | |

PREPARATION 8

2-Methoxy-6-(1-methylbenzimidazol-2-yl)-8-methyl-quinoline

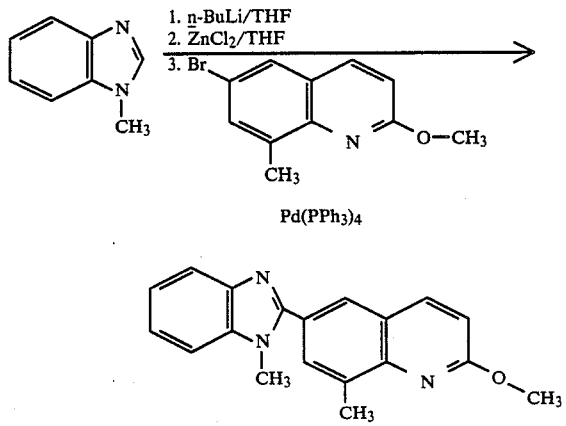

n-Butyllithium (3.55 cm³ of a 1.55M solution in hexane) was added dropwise to a stirred solution of 1-methyl-benzimidazole (0.6 g) in tetrahydrofuran (THF) (10 cm³) at −50° under nitrogen. After 1 hour a solution of anhydrous zinc chloride (1.5 g) in THF (10 cm³) was added and the mixture allowed to warm to room temperature. 2-Methoxy-6-bromo-8-methylquinoline (1.25 g) and tetrakis (triphenylphosphine)palladium (O) (0.05 g) were added and the mixture heated under reflux for 4 hours. Saturated ammonium chloride solution (10 cm³) was added to the cooled mixture, followed by a solution of ethylenediamine tetraacetic acid disodium salt (12.0 g) in water (200 cm³). Ethyl acetate (200 cm³ and methanol (20 cm³) were added and the phase separated. The aqueous layer was further extracted with methanol:dichloromethane; 1:20 by volume (2×200 cm³) and the combined and dried (MgSO₄) organic extracts were evaporated in vacuo to afford a solid which was chromatographed on silica (Merck "MK 60.9385" [Trade Mark]) eluting with methanol:dichloromethane, 1:100 by volume. Combination and evaporation of appropriate fractions gave the title compound (1.05 g) which was characterised spectroscopically and used in Example 4 without further purification.

PREPARATION 9

2-Methoxy-6-(1,5,6-trimethylbenzimidazol-2-yl)-8-methylquinoline, m.p. 167°-168.5°, was prepared similarly to Preparation 8 using 2-methoxy-6-bromo-8-methylquinoline, n-butyllithium, zinc chloride and 1,5,6-trimethylbenzimidazole as starting materials:

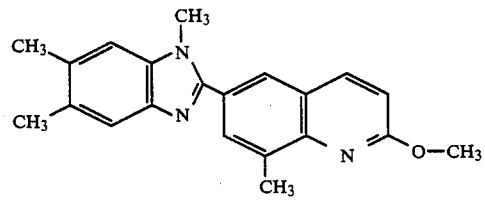

Analysis %: Found: C, 75.8; H, 6.6; N, 12.3; Calculated for $C_{20}H_{19}N_3O$, 0.25 $H_2O$: C, 76.1; H, 6.4; N, 12.7.

PREPARATION 10

1-Bromo-phthalazin-4-one

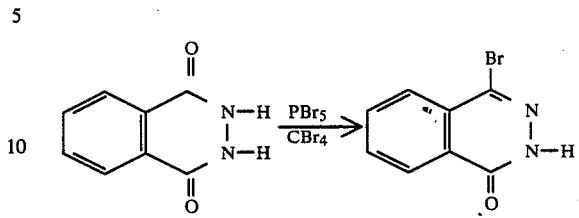

A mixture of phthalhydrazide (3.2 g) and phosphorus pentabromide (19.0 g) was heated with stirring in carbon tetrabromide (50 g) at 125° for 16 hours. The cooled mixture was poured into water (50 cm³) and the product collected by filtration. The solid product was chromatographed on silica (Merck "MK 60.9385" [Trade Mark]) eluting with diethyl ether:dichloromethane, 1:3 by volume. Combination and evaporation of appropriate fractions afforded the title compound, m.p. 268°-271° (1.5 g).

Analysis %: Found: C, 42.1; H, 2.2; N, 12.2; Calculated for $C_8H_5N_2OBr$: C, 42.7; H, 2.2; N, 12.4.

PREPARATION 11

3,3-Dimethyl-5-bromo-indol-2-one

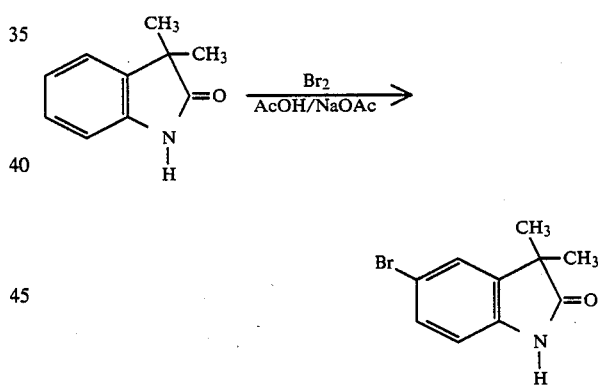

A solution of bromine (1.98 g) in acetic acid (10 cm³) was added dropwise to a stirred solution of 3,3-dimethyl-indol-2-one (2.0 g) and sodium acetate (1.01 g) in acetic acid (10 cm³). The mixture was stirred at room temperature for 30 minutes, poured onto water (20 cm³), basified to pH9 with sodium carbonate, and extracted with ethyl acetate (3×50 cm³). The combined and dried (MgSO₄) organic extracts were evaporated in vacuo and the residue chromatographed on silica (Merck "MK 60.9385" [Trade Mark]) eluting with methanol:hexane:dichloromethane, 1:10:40 by volume. Combination and evaporation of the appropriate fractions gave the title compound, m.p. 166°-166.5° (2.15 g).

Analysis %: Found: C, 49.9; H, 4.2; N, 5.9; Calculated for $C_{10}H_{10}NOBr$: C, 50.0; H, 4.2; N, 5.8.

PREPARATION 12

Trans-1-[4-{ethoxypropenamido)}-3-methylphenyl]-2-methylbenzimidazole

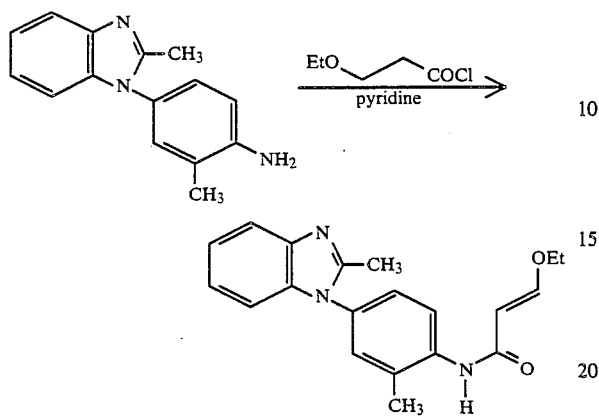

Trans-3-ethoxypropenoyl chloride (1.15 g) was added dropwise to a stirred solution of 1-(3-methyl-4-aminophenyl)-2-methylbenzimidazole (2.0 g) in anhydrous pyridine (12 cm³), cooled to 0° C., and the mixture was warmed to room temperature (20° ). After 1 hour saturated sodium carbonate solution (30 cm³) was added, and the mixture extracted with chloroform (3×100 cm³). The combined and dried (MgSO₄) organic extracts were evaporated in vacuo, and the residue chromatographed on silica (Merck "MK 60.9385" [Trade Mark]) eluting with ethyl acetate. Combination and evaporation of appropriate fractions gave a solid which was recrystallised from ethyl acetate to give the title compound, m.p. 184°-6° (0.25 g).

Analysis %: Found: C, 71.2; H, 6,2; N, 12.5; Calculated for $C_{20}H_{21}N_3O_2$: C, 71.6; H, 6.3; N, 12.5.

PREPARATION 13

1-(3-Methyl-4-aminophenyl)-2-methylbenzimidazole

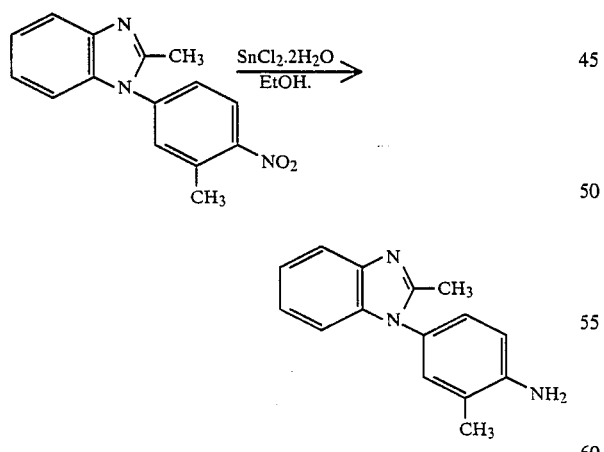

Stannous chloride dihydrate (45.9 g) was added portionwise to a stirred solution of 1-(3-methyl-4-nitrophenyl)-2-methylbenzimidazole (9.2 g) in absolute ethanol (200 cm³) under nitrogen. After heating under reflux for 1 hour, the cooled mixture was basified to pH 9 with aqueous 2.5M sodium hydroxide and extracted with chloroform (3×200 cm³). The combined and dried (MgSO₄) organic extracts were evaporated in vacuo to give the title compound (8.9 g) which was characterised spectroscopically then used directly in Preparation 12 without further purification.

PREPARATION 14

1-(3-Methyl-4-nitrophenyl)-2-methylbenzimidazole

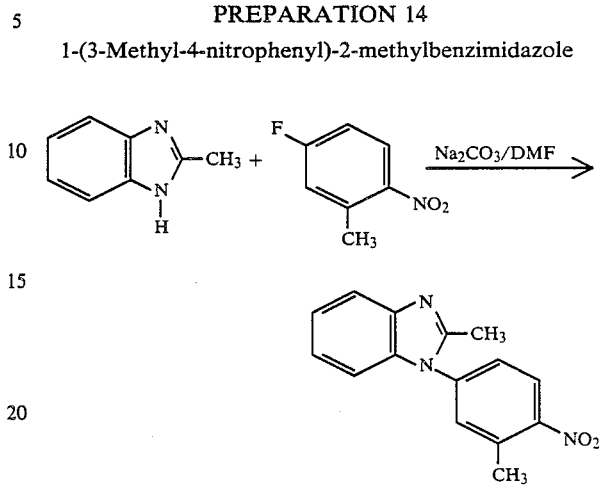

A mixture of 5-fluoro-2-nitrotoluene (10.3 g), 2-methylbenzimidazole (8.7 g) and sodium carbonate (7.5 g) was heated with stirring in dimethylformamide (40 cm³) at 130° for 16 hours under nitrogen. The cooled mixture was evaporated in vacuo, water (50 cm³) added and the mixture extracted with methanol:chloroform, 1:10 by volume. The combined and dried (MgSO₄) organic extracts were evaporated in vacuo to give a residue which was chromatographed on silica (Merck "MK 60.9385" [Trade Mark]) eluting with ethyl acetate. Combination and evaporation of appropriate fractions afforded a solid which was recrystallised from hexane/acetone to give the title compound, m.p. 144°-6°, (10.65 g).

Analysis %:
Found: C, 67.5; H, 4.7; N, 15.6; Calculated for $C_{15}H_{13}N_3O_2$: C, 67.4; H, 4.9; N, 15.7.

PREPARATION 15

2-Methoxy-6-(benzimidazol-2-yl)-8-methylquinoline

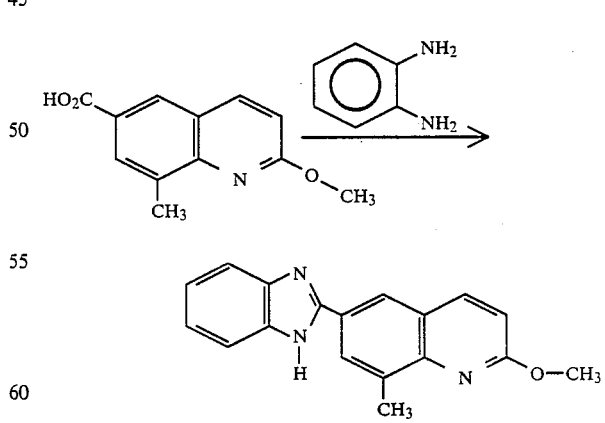

2-Methoxy-8-methylquinoline-6-carboxylic acid (1.09 g) was added in portions to a stirred mixture of o-phenylene diamine (0.54 g) and phosphorus oxychloride (20 cm³) at room temperature (20° ). The mixture was heated under reflux for 4 hours and then solvent was evaporated in vacuo. Ice (20 g) was added to the residue which was then basified to pH 9 with aqueous 2.5M sodium hydroxide and filtered to yield a solid which was chromatographed on silica (Merck "MK 60.9385" [Trade Mark]) eluting with methanol:dichloromethane, 1:100 by volume. Combination and evaporation of appropriate fractions gave the title compound which was characterised spectroscopically and used directly in Example 2 without further purification.

PREPARATION 16

2-Methoxy-6-(2-oxobenzimidazol-1-yl)-8-methylquinoline

This compound, m.p. 280°, was prepared similarly to Example 16 using 2-methoxy-6-[(N-2-aminophenyl)-amino]-8-methylquinoline, and carbonyl diimidazole as starting materials. The product was characterised spectroscopically and used directly in Example 3 without further purification.

PREPARATION 17

2-Methoxy-6-[(N-2-aminophenyl)-amino]-8-methyl-quinoline

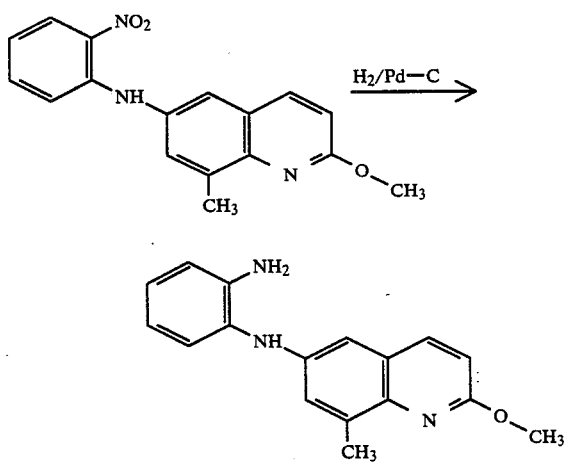

A solution of 2-methoxy-6[(N-2-nitrophenyl)-amino]-8-methylquinoline (0.2 g) in absolute ethanol (20 cm$^3$) was hydrogenated at 60° and 60 p.s.i. (4.13×10$^5$ Pa) pressure over 10% palladised charcoal (0.03 g) for 4 hours. The cooled solution was then filtered through "Solkafloc" (Trade Mark for a cellulose-based filtering aid), evaporated to dryness in vacuo, characterised spectroscopically and used directly in Preparation 16 without further purification.

PREPARATION 18

3,4-Dihydro-4,8-dimethyl-6-[(N-2-aminophenyl)-amino]-2-(1H)-quinolone

This compound, m.p. 195°-199°, was prepared similarly to Preparation 17 using 3,4-dihydro-4,8-dimethyl-6-[(N-2-nitrophenyl)-amino]-2-(1H)-quinolone, hydrogen and palladised charcoal as starting materials. The product was characterised spectroscopically and used directly in Examples 13, 15 and 16 without further purification.

PREPARATION 19

3,4-Dihydro-4,4,8-trimethyl-6-[(N-2-aminophenyl)-amino]-2-(1H)-quinolone

This compound, m.p. 90°, was prepared similarly to Preparation 17 using 3,4-dihydro-4,4,8-trimethyl-6-[(N-2-nitrophenyl)-amino]-2-(1H)-quinolone hydrogen and palladised charcoal as starting materials. The product was characterised spectroscopically and used directly in Example 14.

PREPARATION 20

3,4-Dihydro-4,8-dimethyl-6-[(N-2-nitrophenyl)-amino]-2-(1H)-quinolone, H$_2$O

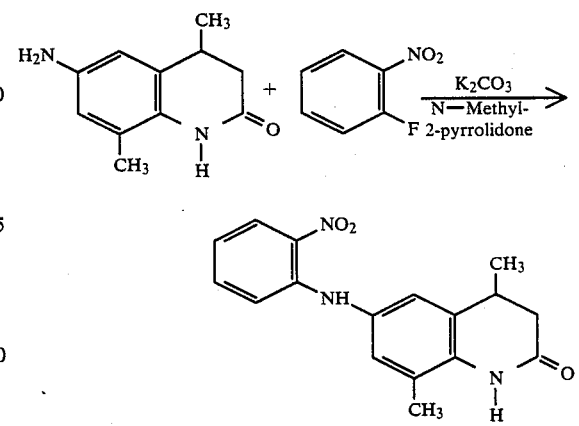

A mixture of 3,4-Dihydro-4,8-dimethyl-6-amino-2-(1H)-quinolone (2.13 g), 1-fluoro-2-nitrobenzene (1.72 g) and sodium carbonate (1.68 g) was heated with stirring in N-methyl-2-pyrrolidone (4 cm$^3$) at 150° for 16 hours under nitrogen. The cooled mixture was partitioned between methanol:dichloromethane, 1:20 by volume (100 cm$^3$) and saturated sodium carbonate solution (50 cm$^3$). The aqueous phase was re-extracted with more methanol:dichloromethane, 1:20 by volume (2×100 cm$^3$) and the combined and dried (MgSO$_4$) organic extracts were evaporated in vacuo to give a solid which was chromatographed on silica (Merck "MK 60.9385" [Trade Mark]) eluting with ethyl acetate. Combination and evaporation of appropriate fractions afforded the title compound which was characterised spectroscopically and used directly in Preparation 18 without further purification.

PREPARATION 21

2-Methoxy-6-[(N-2-nitrophenyl)-amino]-8-methyl-quinoline

This compound, m.p. 185°, was prepared similarly to Preparation 20 using 2-methoxy-6-amino-8-methylquinoline, 1-fluoro-2-nitrobenzene, and sodium carbonate as starting materials. The product was characterised spectroscopically and used directly in Preparation 17 without further purification.

PREPARATION 22

3,4-Dihydro-4,8,8-trimethyl-6-[(N-2-nitrophenyl)-amino]-2-(1H)-quinolone

This compound, m.p. 205°14 211°, was prepared similarly to Preparation 20 using 3,4-dihydro-4,8,8-trimethyl-6-amino-2-(1H)-quinolone, 1-fluoro-2-nitrobenzene, and sodium carbonate as starting materials.

Analysis %: Found: C, 65.5; H, 6.0; N, 13.0; Calculated for $C_{18}H_{19}N_3O_3$: C, 65.5; H, 6.0; N, 12.7.

PREPARATION 23

3,4-Dihydro-4-methyl-6-amino-8-methyl-2-(1H)-quinolone

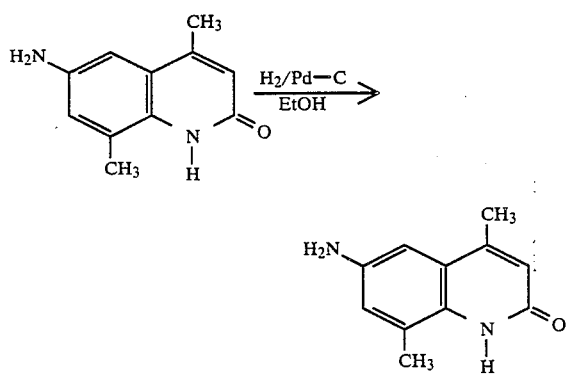

A suspension of 4-methyl-6-amino-8-methyl-2-(1H)-quinolone (0.38 g) in absolute ethanol (50 cm³) was hydrogenated at 100° and 2000 p.s.i. (13.7×10⁶ Pa) pressure over 10% palladised charcoal (0.05 g) for 72 hours. The cooled solution was then filtered through "Solkafloc" (Trade mark for a cellulose-base filtering aid) and evaporated in vacuo to give a solid which was chromtographed on silica (Merck "MK 60.9385" [Trade Mark]) eluting with methanol:chloroform, 1:50 by volume. Combination and evaporation of appropriate fractions gave a residue which on trituration with ethyl acetate afforded the title compound, m.p. 207°–10°, (0.22 g).

Analysis %: Found: C, 68.9; H, 7.5; N, 14.2; Calculated for $C_{11}H_{14}N_2O$: C, 69.4; H, 7.4; N, 14.7.

PREPARATION 24

3,4-Dihydro-4,4-dimethyl-6-amino-8-methyl-2-(1H)-quinolone

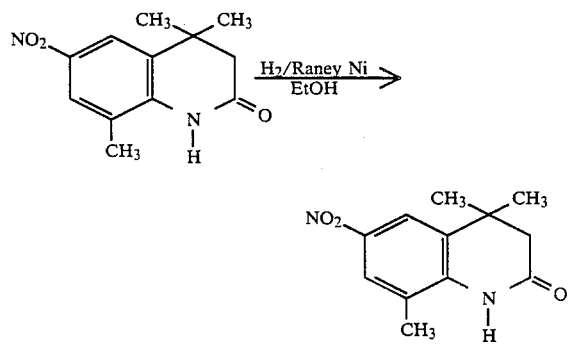

A solution of 3,4-dihydro-4,4-dimethyl-6-nitro-8-methyl-2-(1H)-quinolone (9.46 g) in absolute ethanol (80 cm³) was hydrogenated at 60° and 60 p.s.i. (4.13×10⁵ Pa) pressure over Raney nickel (0.9 g) for 6 hours. The cooled solution was then filtered through "Solkafloc" (Trade mark for a cellulose based filtering aid) and evaporated in vacuo to give a solid which was chromatographed on silica (Merck "MK 60.9385" [Trade Mark]) eluting with methanol:chloroform, 1:33 by volume. Combination and evaporation of appropriate fractions gave the title compound (3.17 g) which was characterised spectroscopically and used directly in Preparation 22 without further purification.

Preparation 25

3,4-Dihydro-4,4,8-trimethyl-6-nitro-2-(1H)-quinolone

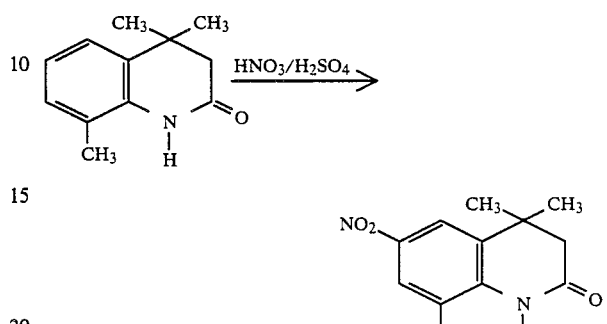

A mixture of concentrated nitric acid (10 cm³, S.G.=1.42) and 98% w/w sulphuric acid (25 cm³) was added dropwise to a stirred solution of 3,4-dihydro-4,4,8-trimethyl-2-(1H)-quinolone (6 g) in 98% w/w sulphuric acid (25 cm³) cooled to −10°. The temperature was maintained at −10° for a further 30 minutes, the mixture poured onto ice (200 g), basified to pH 9 with saturated sodium carbonate solution and extracted with methanol:chloroform, 1:20 by volume (2×300 cm³). The combined and dried (MgSO₄) organic extracts were evaporated in vacuo to give the title compound (6.46 g) which was characterised spectroscopically and used directly in Preparation 24 without further purification.

PREPARATION 26

3,4-Dihydro-4,4,8-trimethyl-2-(1H)-quinolone

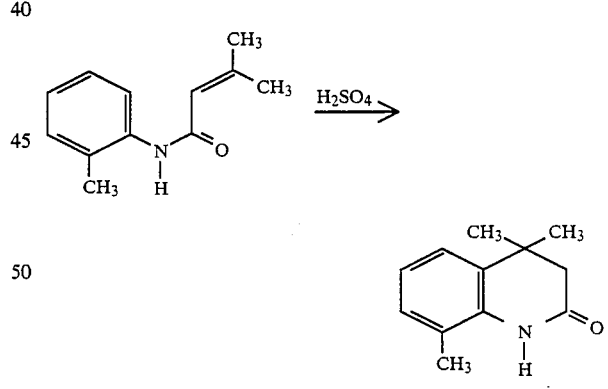

N-(1-oxo-3-methyl-but-2-en-yl)-2-methylaniline (0.5 g) was added with stirring to 98% w/w sulphuric acid (10 cm³) at 0°. After 2 hours at room temperature (20°) the mixture was poured carefully onto ice (30 g) and the resulting solution was basified to pH 9 with saturated carbonate solution. The mixture was then extracted wilth dichloromethane (2×200 cm³), and the combined and dried (MgSO₄) organic extracts were evaporated in vacuo to give a solid which was chromatographed on silica (Merck "MK 60.9385" [Trade mark]). Elution with dichloromethane, followed by combination and evaporation of appropriate fractions gave the title compound, m.p. 120° (0.21 g).

Analysis %: Found: C, 75.3; H, 7.7; N, 7.3; Calculated for $C_{12}H_{15}NO$: C, 75.1; H, 7.7; N, 7.4.

PREPARATION 27

N-(1-Oxo-3-methylbut-2-en-yl)-2-methylaniline

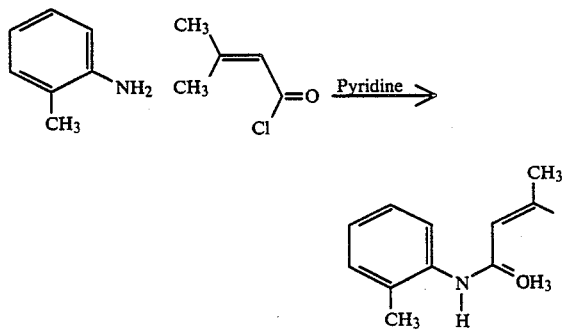

3-Methylbut-2-en-oylchloride (24.2 g) was added dropwise to a stirred solution of 2-methylaniline (20 g) in anhydrous pyridine (200 cm³) cooled to 0°. After 1 hour solvent was evaporated in vacuo to yield a solid which was recrystallised from ether/petroleum ether (boiling range 40-60) to afford the title compound, m.p. 105 (29.5 g).

Analysis: Found: C, 75.2; H, 7.9; N, 7.4; Calculated for $C_{12}H_{15}NO$: C, 75.1; H, 8.0; N, 7.4.

We claim:

1. A heterobicyclic-substituted 2-(1H)-quinolone compound of the formula:

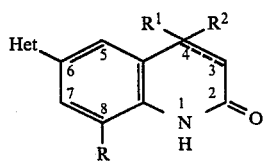

or a pharmaceutically acceptable salt thereof, wherein
Het is a 1(H)-imidazo(4,5-b)pyridin-6-yl group, said heterobicyclic-substituted 2-(1H)-quinolone compound being optionally substituted on the available ring carbon atoms in one or both of the rings of Het with up to three $C_1$-$C_4$ alkyl groups and being additionally optionally substituted on the sole available ring carbon atom in the imidazo portion of Het with one oxo group;
R is hydrogen or $C_1$-$C_4$ alkyl; and
$R^1$ and $R^2$ are each independently hydrogen or $C_1$-$C_4$ alkyl; and the dashed line between the 3- and 4-positions represents an optional bond in which case $R^2$ is absent.

2. A compound as claimed in claim 1 wherein the $C_1$-$C_4$ alkyl group optionally substituted on the available ring carbon atoms of Het is methyl.

3. A compound as claimed in claim 1 wherein Het is a 1(H)-imidazo(4,5-b)pyridin-6-yl or 2-oxoimidazo(4,5-b)pyridin-6-yl group; and R, $R^1$ and $R^2$ are each hydrogen or methyl, with said $R^2$ being absent when the dashed line represents an optional bond.

4. A compound as claimed in claim 1 having the formula:

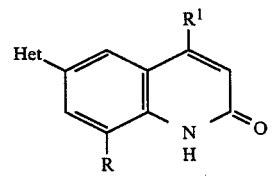

wherein Het is a 1(H)-imidazo(4,5-b)pyridin-6-yl or 2-oxoimidazo(4,5-b)pyridin-6-yl group; and R and $R^1$ are each hydrogen or methyl.

5. A compound as claimed in claim 4 wherein Het is 1(H)-imidazo[4,5-b]pyridin-6-yl, R is methyl and $R^1$ is hydrogen.

6. A compound as claimed in claim 4 wherein Het is 2-oxoimidazo[4,5-b]pyridin-6-yl, R is methyl and $R^1$ is hydrogen.

7. 6-{(1H)-Imidazo[4,5-b]pyridin-6-yl}-8-methyl-2-(1H)-quinolone.

8. A pharmaceutical composition comprising a pharmaceutically acceptable carrier or diluent and an effective cardiac stimulating amount of a compound as claimed in claim 1.

9. The composition according to claim 8 wherein the compound is 6-{(1H)-imidazo[4,5-b]pyridin-6-yl}-8-methyl-2-(1H)-quinolone.

10. A method for stimulating cardiac activity in the treatment of a subject afflicted with congestive heart failure, which comprises administering to said subject an effective cardiac stimulating amount of a compound as claimed in claim 1.

* * * * *